(12) United States Patent
Kirk

(10) Patent No.: US 6,416,497 B1
(45) Date of Patent: Jul. 9, 2002

(54) NEEDLE PROTECTION HOLDER

(75) Inventor: Kevin F. Kirk, Walled Lake, MI (US)

(73) Assignee: Dispomedic 2000 Ltd. (IL)

( * ) Notice: Subject to any disclaimer, the term of this patent is extended or adjusted under 35 U.S.C. 154(b) by 0 days.

(21) Appl. No.: 09/384,483

(22) Filed: Aug. 27, 1999

(51) Int. Cl.$^7$ ................................................. A61M 5/32
(52) U.S. Cl. ...................................... 604/198; 128/919
(58) Field of Search ................................ 604/110, 187, 604/192, 197, 198, 263; 128/919

(56) References Cited

U.S. PATENT DOCUMENTS

| | | |
|---|---|---|
| 4,752,292 A | 6/1988 | Lopez et al. |
| 4,795,432 A | 1/1989 | Karczmer |
| 4,850,961 A | 7/1989 | Wanderer et al. |
| 4,850,977 A | 7/1989 | Bayless |
| 4,927,416 A | 5/1990 | Tomkiel |
| 5,030,209 A | 7/1991 | Wanderer et al. |
| 5,106,379 A | 4/1992 | Leap |
| 5,135,510 A | 8/1992 | Maszkiewicz et al. |
| 5,147,326 A | 9/1992 | Talonn et al. |
| 5,219,333 A | 6/1993 | Sagstetter et al. |
| 5,242,416 A | 9/1993 | Hutson |
| 5,300,039 A | 4/1994 | Poulsen |
| 5,336,187 A | 8/1994 | Terry et al. |
| 5,346,480 A | 9/1994 | Hess et al. |
| 5,364,362 A | 11/1994 | Schulz |
| 5,368,568 A | 11/1994 | Pitts et al. |
| 5,376,080 A | 12/1994 | Petrussa |
| 5,385,551 A | 1/1995 | Shaw |
| 5,403,286 A | 4/1995 | Lockwood, Jr. |
| 5,423,758 A | 6/1995 | Shaw |
| 5,433,712 A | 7/1995 | Stiles et al. |
| 5,514,107 A | 5/1996 | Haber et al. |
| 5,527,284 A | 6/1996 | Ohnemus et al. |
| 5,527,294 A | 6/1996 | Weatherford et al. |
| 5,531,694 A | 7/1996 | Clemens et al. |
| 5,549,558 A | 8/1996 | Martin |
| 5,562,624 A | 10/1996 | Righi et al. |
| 5,578,011 A | 11/1996 | Shaw |
| 5,591,138 A | 1/1997 | Vaillancourt |
| 5,613,952 A | 3/1997 | Pressly, Sr. et al. |
| 5,632,732 A | 5/1997 | Szabo et al. |
| 5,632,733 A | 5/1997 | Shaw |
| 5,634,909 A | 6/1997 | Schmitz |
| 5,681,292 A | 10/1997 | Tober et al. |
| 5,695,474 A | 12/1997 | Daugherty |
| 5,695,475 A | 12/1997 | Best, Jr. et al. |
| 5,695,476 A | 12/1997 | Harris |
| 5,938,644 A * | 8/1999 | Kirk |

* cited by examiner

Primary Examiner—Richard K. Seidel
Assistant Examiner—LoAn H. Thanh
(74) Attorney, Agent, or Firm—Dykema Gossett PLLC

(57) ABSTRACT

The needle protection holder encloses an automatically retractable safety syringe and needle within a tubular cylinder after the needle has been used. Its intended purpose is to remove a needle attached to a syringe from a patient, both human and animal, thereby containing the needle safely within the holder or cylinder. With such a construction, the holder prevents the exchange of bodily fluids caused by needle sticks which are known to cause serious illnesses including death to medical technicians and personnel.

47 Claims, 5 Drawing Sheets

NEEDLE PROTECTION HOLDER

FIELD OF THE INVENTION

The present invention relates generally to the art of fully automated retractable safety syringes and more particularly to needle protection assemblies or shielding devices for syringes in order to reduce the likelihood of unintentional puncture of human beings and animals.

RELATED U.S. PATENT

The present invention is an improvement over my U.S. Pat. No. 5,938,644 entitled "Needle Protection Holder", which issued Aug. 17, 1999. Specifically, the improvements are directed to the thumb latch and to the washer construction equipped with a Luer-Lock, Luer-slip male and female attachment that are standardized by the International Standards Organization and by the American Standards National Institute to fit all Luer-Lock and Luer-slip tipped syringes thereby turning the products into fully automated retractable safety syringes.

DESCRIPTION OF THE PRIOR ART

The spread of Acquired Immune Deficiency Syndrome or AIDS in the 1980's has greatly increased the concern of health care providers over the spread of communicable diseases through accidental needle pricks or punctures. Health care personnel including nurses, doctors and other providers accidentally prick themselves with needles on an average of two or more times a year. With the increase in AIDS, the chance of a health care provider being pricked by an AIDS contaminated needle over a period of years has become quite high and of great concern not only to health care personnel but also to government officials. In addition, other severe but less deadly diseases are known, such as hepatitis, which are transmitted through contaminated needle pricks or punctures. Such punctures occur in many ways, such as a nurse tripping while carrying a used and exposed needle or even while trying to cap a used needle.

Consequently, a greater need has developed for shielding devices or protection devices for needles of syringes such that the shielding devices are effective, easy to use and require only minor modifications to allow use with conventional types of syringes of the disposable and non-disposable types. Numerous devices have been developed to reduce the risk of accidental needle pricks.

Many of these devices include a cylindrical sheath secured to the syringe which may be telescopically advanced and retracted to enclose and expose the needle of the syringe. The currently available shielding devices that provide a cylindrical sheath to telescopically encircle the needle of a syringe suffer several deficiencies or shortcomings. Many of the existing devices require an operator such as a doctor, nurse or technician to use both hands to position the protection sheath in encircling relation with the syringe needle thereby increasing the likelihood of accidental needle pricks. Thus, when the user reaches with one hand to extend the sheath of the syringe, the medical attendant accidentally sticks the free hand through carelessness, being bumped or the like.

In many of the existing devices, the protective sheaths cannot be locked in encircling relationship with the syringe needle possibly resulting in accidental needle pricks if a compressed force is inadvertently applied to the protective sheath of the syringe. In other existing devices, the protective sheath permanently locks in protective relation with the syringe needle when advanced thereto preventing immediate protection of the syringe needle where the syringe must be used more than once for a given procedure. Existing sheathing devices also tend to require major modifications to existing syringes or greatly interfere with the normal use of the syringe.

SUMMARY OF THE INVENTION

It is a feature of the present invention to provide a novel needle protection holder or assembly for various types of syringes which minimizes the likelihood of accidental puncture.

Another feature of the present invention is to provide a needle protection holder for a syringe which, after utilization, isolates the used needle within the holder so as to render such needle harmless.

Still another feature of the present invention is to provide a needle protection holder or assembly for a syringe which is operable utilizing only one hand thereby permitting the other hand of the medical technician to be used for other purposes.

A still further feature of the present invention is to provide a needle protection holder or assembly for a syringe which includes a spring which is compressed during the injection of the fluid in the syringe into the patient whereafter the compressed spring is released which is effective to retract into the interior of the holder the needle to prevent its reuse.

Still another feather of the present invention is to provide a needle protection holder which is adaptable to various types of syringes including standard syringes and Luer Lock syringes, which is economical to manufacture and is efficient to use while preventing accidental punctures of humans and animals.

These as well as other features are accomplished by providing a device that encloses a syringe and needle within a tubular shell after the needle has been used. Its intended purpose is to remove the needle attached to a syringe from a patient, both human and animal, thereby containing the needle safely within its casing or housing. The needle protection holder disallows the exchange of bodily fluids caused by needle sticks or punctures. Such punctures can result in severe illness including death and such risk can be deterred by using the present invention.

A further feature of the present invention is that the needle protection holder or syringe retractor assembly can be manufactured in different sizes to fit virtually any Luer Lock, Luer-slip male and female attachments or regular point syringes on the market. Thus, the present invention will permit hospitals and clinics to select any standard brand of syringe to use with the needle protection holder of the present invention. A medical institution can use the needle protection holder along with its own brands of standard syringes, thereby preserving the institution's ability to meet financial goals while providing employees with a safe environment and peace of mind knowing that accidental punctures have been greatly diminished or eliminated.

While the needle protection holder or syringe retractor of the present invention is intended for single usage, a medical technician could, if needed, unlock its mechanism and reuse the same syringe. This could prove useful in situations where multiple usage of a syringe is required such as in the administration of numbing or pain killing drugs to the same patient. This needle protection holder or device appears to be the first device to fit and lock onto a Luer Lock and onto a regular point syringe. A feature of the present invention is the provision of an attachment washer which is designed to connect a syringe and a needle utilizing the same method currently used to connect a syringe and a needle together. The Luer Lock and regular point syringe are two of the most common syringes currently used by hospitals and by veterinary clinics and would, therefore, provide a great deal of risk management protection. Thus, the needle protection holder or syringe retractor or device has been designed so that the medical technician can manipulate it with only one hand thereby freeing up the technicians other hand for other vital medical operations. It is well known that time can make the difference between life and death in many medical situations and can also effect the efficiency in which the medical technician cares for his or her own safety. With the present invention, virtually no time is lost in preparing the device for use; assembly takes only a matter of a few seconds to complete. Once the technician has administered the injection, the touch of the spring biased latch causes the needle to retract safely within the constraints of the tubular housing.

Another feature of the present invention is to provide a needle protection holder with a novel thumb latch mounted on the cylinder, a pair of spaced apart stop pedestals are provided on the cylinder and are provided with axles below the stop pedestals. The thumb latch has an integral lip opposite the longitudinal axis of the cylinder and a pair of spaced apart arms rotatably carried by the axles whereby when the latch is rotated in one direction about the axles towards the longitudinal axis it causes the lip to engage the syringe contained in the cylinder and thereby retain and latch the syringe in place.

Still another feature of the present invention is to provide a needle protection holder wherein the thumb latch when rotated in the opposite direction away from the longitudinal axis about the axles cause the lip to disengage from the syringe and the thumb latch to move away from the cylinder in an amount limited by the engagement of the thumb latch with the stop pedestals.

A further feature of the present invention is to provide a needle protection holder wherein the thumb latch has a curved surface for a person's thumb when operating the latch, with the lip being an integral part of the latch and being inclined downwardly towards the open end of the cylinder.

A still further feature of the present invention is to provide a needle protection holder wherein the thumb latch is provided with an integral downwardly extending spring located between the spaced apart arms, with the spring being engageable with the exterior surface of the cylinder wall and providing pressure on the thumb latch so that the locking of the syringe in the down position can take place.

A still further feature of the present invention is to provide a needle protection holder wherein the thumb latch including the arms, lip and spring are molded as an integral unit from a plastic material.

Another feature of the present invention is to provide a needle protection holder where the stop pedestals are formed out of the walls of the cylinder holding the axles.

Still another feature of the present invention is to provide a needle protection holder wherein the spring is flat and of generally rectangular cross-section and glides on the exterior surface of the cylinder.

A further feature of the present invention is to provide a needle protection holder wherein the axles are aligned directly under the lip of the thumb latch.

A still further feature of the present invention is to provide a needle protection holder wherein the arms of the thumb latch are provided with openings so that the arms when pressure is applied to the arms, the openings receive the axles.

A still further feature of the present invention is to provide a needle protection holder wherein the inner edges of the arms are beveled to remove materials and thereby facilitate the mounting of the thumb latch on the axles.

Another feature of the present invention is to provide a needle protection holder for a fully automated retractable safety syringe, with the holder containing a generally cylindrical washer with four circumferentially spaced apart arms provided on their outer unattached ends with radially outwardly extending protrusions or buttons. The protrusions have matching elongated channels and matching elongated openings or slots on the interior surface of the cylinder extending through the wall of the cylinder, with the protrusions, channels and elongated openings cooperating to maintain the orientation of the washer in the cylinder.

Still another feature of the present invention is to provide a needle protection holder wherein the arms of the washer are provided with first and second pairs of arms, each arm being integrally connected on one end of the washer, with the first pair of arms being located 180° apart, with the second pair of arms being located 180° apart, with the cylinder wall having a pair of elongated openings for receiving the outwardly extending protrusions thereby preventing the movement of the washer towards one end of the cylinder and preventing the washer and the syringe and needle from existing the cylinder when an upward thrust is applied to the washer.

A further feature of the present invention is to provide a needle protection holder wherein each of the protrusions or buttons has a top surface, a pair of side surfaces, an outer surface and a bottom surface, with the top surface being angled upwardly to facilitate the movement of the protrusion into the corresponding elongated opening in the cylinder and thereby catch and hold the washer in position in the elongated openings.

A still further feature of the present invention is to provide a needle protection holder wherein the bottom surface is inclined upwardly to permit the washer to move towards the bottom wall of the cylinder without catching in the elongated openings.

Another feature of the present invention is to provide a needle protection holder wherein the elongated openings are offset from the center and the protrusions or buttons are offset from the center line of the first pair of arms.

Still another feature of the present invention is to provide a needle protection holder wherein each of the arms of the second pair has a center line, with the second arms having outwardly projecting protrusions or buttons which are symmetrically arranged on the center lines thereof, with the cylinder wall between the ends having a second pair of elongated openings for receiving the protrusions or buttons of the second arms for stopping downward movement and unlocking of the washer when required so that downward movement of the washer can occur.

Still another feature of the present invention is to provide a needle protection holder wherein the second pair of elongated openings in the cylinder wall are in the form of T-shaped slots, with the protrusions or buttons of the second pair of arms when received in the T-shaped slots preventing the washer from being pushed downwardly into the bottom of the cylinder.

A further feature of the present invention is to provide a needle protection holder wherein the cylinder is provided with a pair of elongated flexible release arms which overly the T-shaped slots, the release arms when inward pressure is applied thereto engaging the protrusions or buttons of the second pair of arms to disengage the protrusions from the T-shaped slots thereby permitting manual pressure to be applied to the syringe to move the washer, syringe and needle downwardly into the bottom of the cylinder, where the syringe is locked in the down position by the thumb latch.

Other advantages and features of the present invention shall become apparent from the following detailed description of the preferred embodiment thereof, when taken in conjunction with the drawings wherein like reference characters refer to corresponding parts in the several views.

The drawings constitute a part of this specification and include an exemplary embodiment of the present invention and illustrate various features thereof.

DETAILED DESCRIPTION OF THE PREFERRED EMBODIMENT

Referring now to the drawings, the needle protection holder is designated by the numeral 10 and is designed to be interposed between a hypodermic syringe 12 and a needle 14 (FIGS. 8–11 inclusive). The holder 10 comprises an elongated cylinder, tube or main housing unit 16 having an elongated extending axis 18. The holder is made from a clear plastic material.

Figures 4, 5, 6, 7:
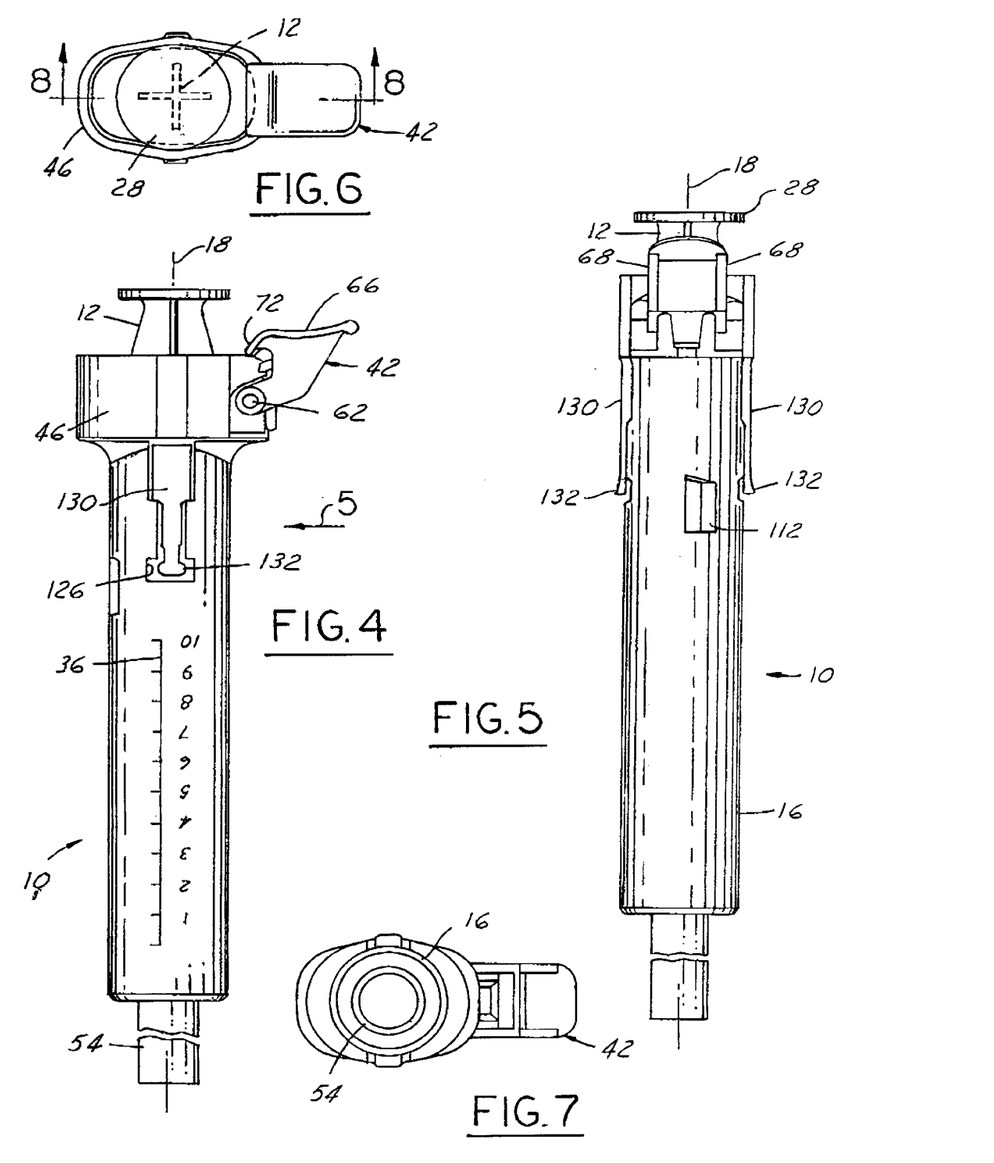
FIG. 4 is an elevational side view of the needle protection holder and syringe, with parts broken away and in a locked position ready for use.
FIG. 5 is a side elevation of the needle protection holder and syringe looking in the direction of arrow 5 of FIG. 4.
FIG. 6 is a top view of the needle protection holder and syringe of FIG. 4.
FIG. 7 is a bottom view of the needle protection holder and syringe of FIG. 4.

The syringe 12 is a conventional disposable or nondisposable hypodermic syringe having a Luer Lock coupling 20 and a needle hub 22 at the needle end of the syringe housing, cylinder or barrel 24. The barrel 24 of the syringe 12 at the other end is open and receives a conventional plunger 26 having a thumb rest 28 at one end and a piston-like element 30 attached thereto at the other end. The plunger 26 moves up and down within the syringe barrel 24 when pressure is applied to the thumb rest 28 of the plunger and to thereby dispense fluid from the syringe 12 through the needle 14. The open end of the barrel 24 is provided with a finger flange 32. The outer surface 34 of the barrel 24 is provided with suitable graduations 36 which can be viewed through the clear plastic holder 10 in FIGS. 1 and 4. Such graduations are used on the syringe 12 to indicate the capacity of the medication to be administered.

Figure 8:
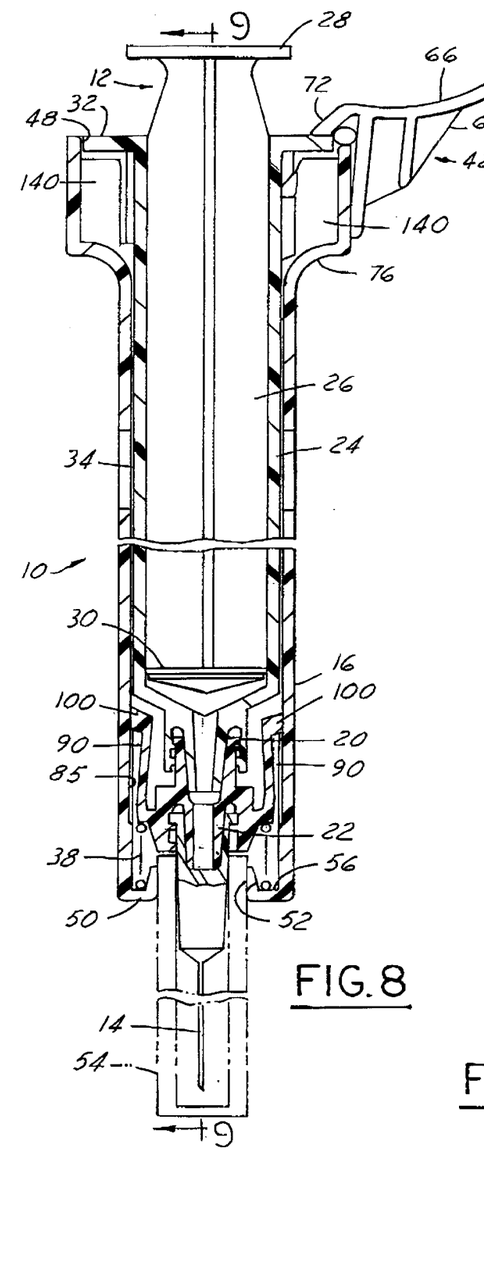
FIG. 8 is a cross sectional view taken on the line 8—8 of FIG. 6 and showing the syringe in a latched position.
Figure 9:
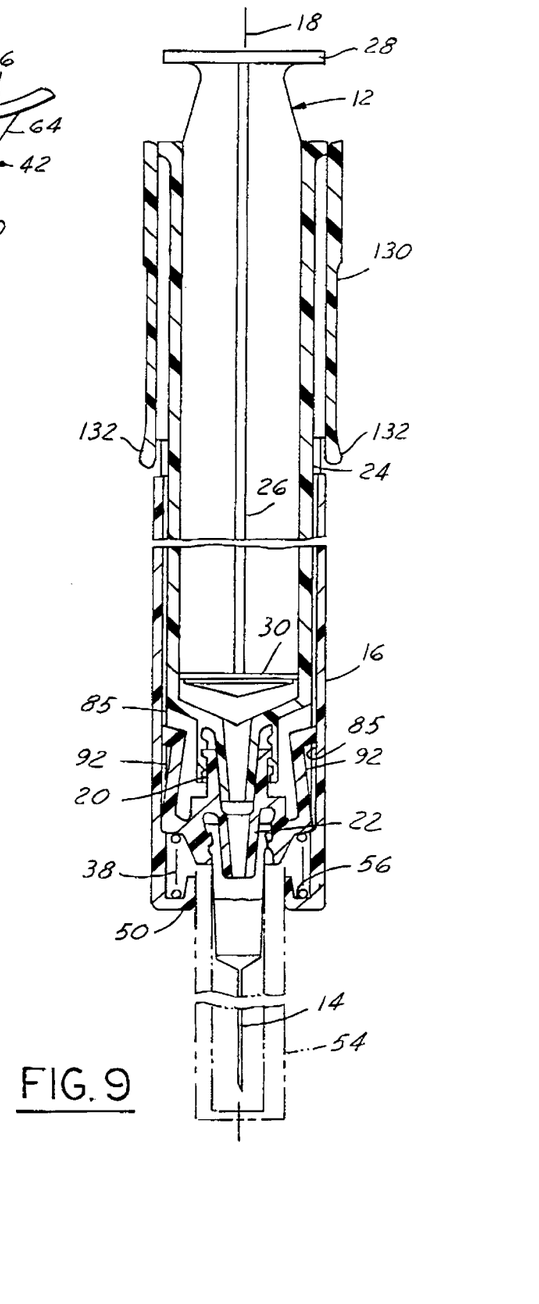
FIG. 9 is a cross sectional view taken on the line 9—9 of FIG. 8 and showing the syringe in a latched position.
Figure 10:
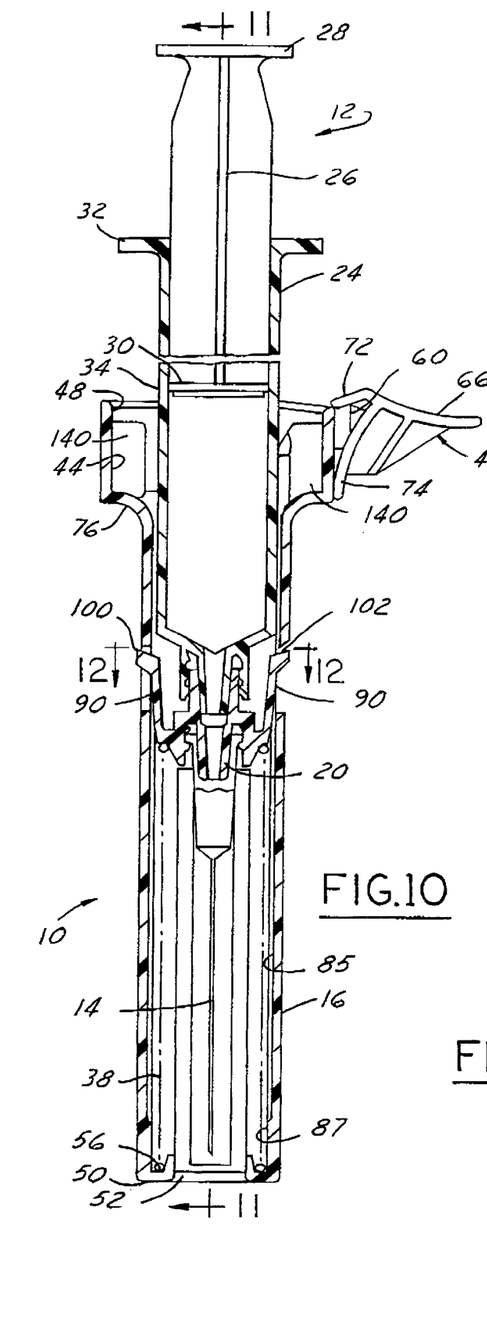
FIG. 10 is a cross sectional view of the needle protection holder and syringe in an unlatched position, with the needle contained within the cylinder.
Figure 11:
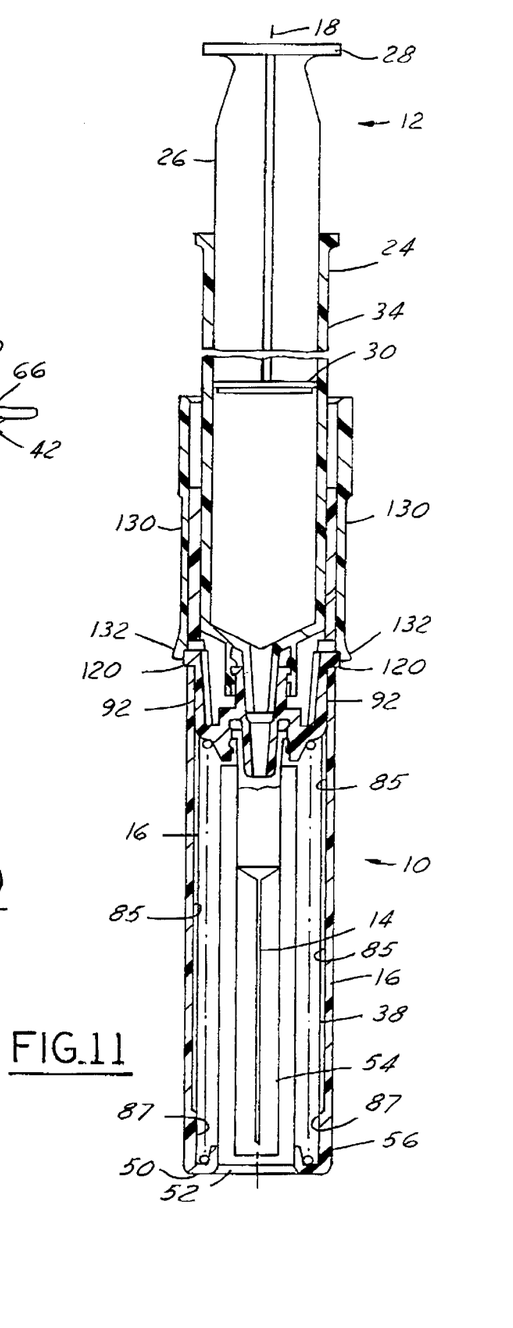
FIG. 11 is a cross sectional view taken on the line 11—11 of FIG. 10.
Figure 12:
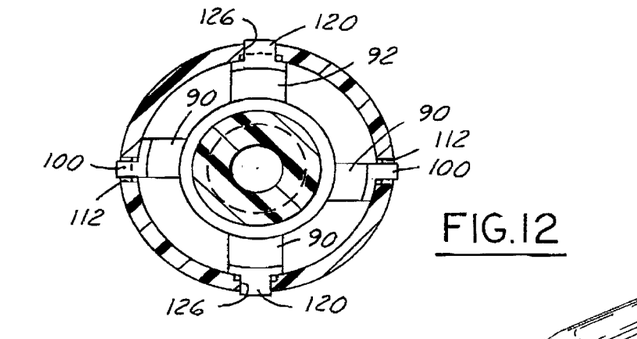
FIG. 12 is a cross sectional view taken on the line 12—12 of FIG. 10.
Figure 13:
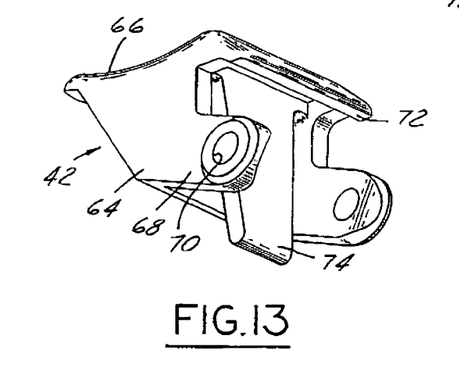
FIG. 13 is a perspective view of the thumb latch illustrating the integral lip, spaced apart arms and integral spring.
Figure 14:
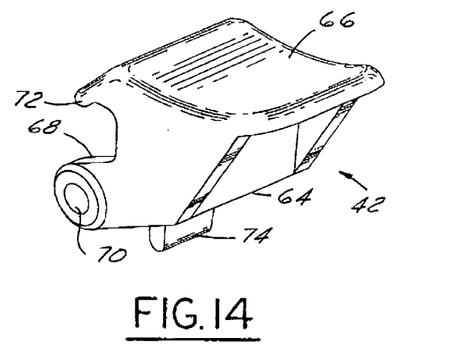
FIG. 14 is another perspective view of the thumb latch taken from a different direction and illustrating the curved thumb rest and other side thereof.

The needle protection holder 10, excluding the hypodermic syringe 12 and needle 14, includes the main housing, tube or cylinder 16, and a compression spring 38 shown in an expanded or extended position in FIGS. 10 and 11 and in a compressed position in FIGS. 8 and 9. The needle protection holder 10 further includes an improved unitary washer or washer assembly 40 and a unique thumb latch 42.

The upper end of the elongated cylinder 16 is open and is enlarged to provide an oval-like entrance 44 to the cylinder or tube 16. The enlarged oval entrance 44 has various curves and/or flat surfaces 46 terminating at the entrance by the ring-like rim 48. The other end of the cylinder 16 has an inwardly turned flange providing a bottom wall 50. The bottom wall 50 has an opening 52 through which the needle 14 and the needle cap 54 may extend as illustrated in FIGS. 8 and 9. The bottom wall 50 and the interior thereof provides a spring seat 56 for the compression spring 38 as illustrated in FIGS. 8 and 9.

The oval surface or wall 46 provided at the enlarged mouth of the cylinder 16 has a pair of stop pedestals 60 (FIGS. 3 and 10) which are formed out or struck out of the walls of the oval wall 46. The purpose of the stop pedestals 60 as will subsequently appear is to prevent the thumb latch 42 from traveling too far outwardly away from the longitudinal axis 18 of the cylinder 16. The exterior of the oval wall 46 is provided with a pair of axles 62. The axles 62 are located generally directly below the stop pedestals 60. The stop pedestals 60 are formed out of the walls 46 of the cylinder 16 to which the axles 62 are connected.

The thumb latch 42 has an integral body 64 made from a plastic material. The top surface of the thumb latch 42 is provided with a curved area 66 upon which the thumb of the user rests when operating the syringe 12. The thumb latch 42 further includes a pair of integral laterally spaced apart arms 68, the outer or free ends of the arms 68 each being provided with an opening 70 for receiving an axle 62. The one-piece plastic molding or thumb latch 42 further includes a downwardly extending rim or lip 72 that causes the latch 42 to catch and stop when the latch 42 stops. The lip is molded into the underside of the thumb latch 42.

The unitary thumb latch 42 includes a resistance spring 74 that is built into the thumb latch 42. The spring 74 is elongated and of generally rectangular cross-section. The plastic material used to make the thumb latch 42 is taken from the group of plastic including polypropylene and Nylon. The underside of the oval-like entrance 44 to the cylinder 16 is provided with a finger hold or surface 76 which a person grips with the fingers when applying thumb pressure to the thumb rest 28 of the plunger 26.

With respect to the use and functioning of the novel thumb latch 42, the stop pedestals 60 which are struck out from the walls of the cylinder 16 (FIG. 3) are provided to provide pivot points, elements or axles 62. One axle or pivot point 62 is located below each of the stop pedestals 60. This feature ensures that the built-in spring 74 of the thumb latch 42 does not extend past the points where the finger rest or surface 76 begins as shown in FIG. 8. Specifically, the resistance spring 74 which guides smoothly on the surface 46 adjacent the entrance to the cylinder 16 applies pressure thereto (FIG. 10) as the thumb latch 42 travels away from the longitudinal axis 18 of the cylinder 16. At such time the thumb latch 42, specifically the lip 72, engages the stop pedestals 60 as shown in FIG. 10 thereby preventing the thumb latch from rotating further away from the center axis 18. The spring 74 assists in stabilizing the lateral movement of the thumb latch 42 about the hinge or pivot points or axles 62. As mentioned previously, the resistance spring 74 when the thumb latch 42 is moved in the opposite direction towards the longitudinal axis 18 of the cylinder 16 provides pressure on the thumb latch 42 so that the locking of the syringe 12 in the downward position can take place as viewed in FIGS. 1, 4 and 8.

Figures 1, 2, 3:
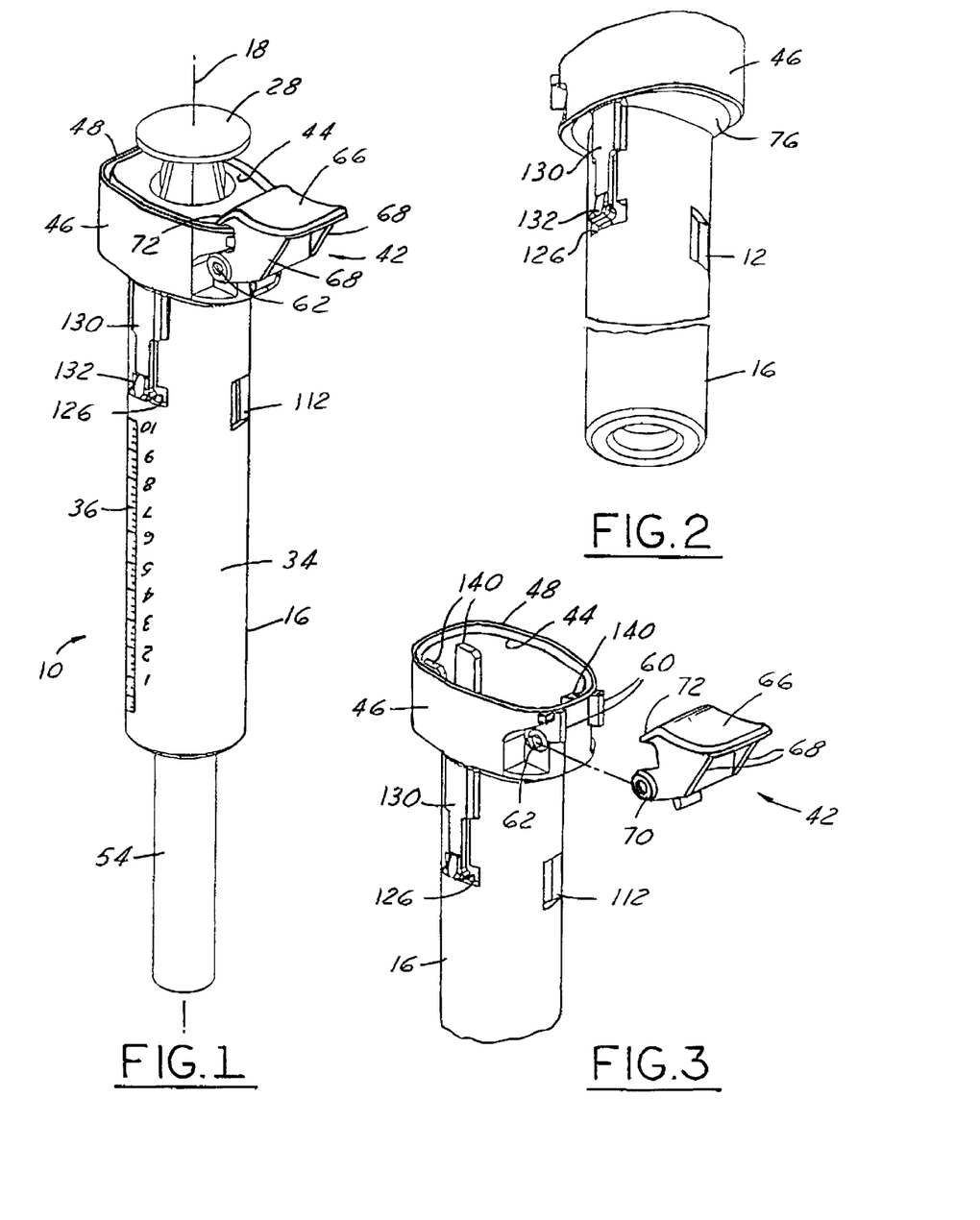
FIG. 1 is a perspective view of the syringe and the needle protection holder with the syringe plunger and the needle covered by a safety cap in a latched position ready for use.
FIG. 2 is a fragmentary perspective view of the needle protection holder with parts broken away.
FIG. 3 is a fragmentary perspective view of the needle protection holder with parts broken away and showing the structure for mounting the thumb latch on the axles of the cylinder.

Specifically, the pivot points or axles 62 protrude outwardly from the main cylinder or housing 16 at a 90° angle from the position of the thumb latch 42. Such pivot points or axles 62 are located near the center axis 18 of the cylinder 16 and are aligned or located directly under the holding lip 72 of the thumb latch 42 as illustrated in FIG. 1. The purpose of the relationship between the axles or pivot 62 and the lip 72 of the thumb latch 42 is to maximize the holding ability of the thumb latch 42 when upward pressure is applied to it by the compression spring 38 of the hypodermic syringe 12 when located in the locked or down position shown in FIGS. 1, 8 and 9.

To attach the thumb latch 42 to the main cylinder housing 16, pressure is merely applied to the arms 68 of the thumb latch 42 with the result that the arms 68 snap onto the axles 62 by means of the corresponding holes or openings 70 provided in the arms. The pair of spaced apart arms 68 of the thumb latch 42 have the ends adjacent the openings 70 beveled at the inner edges to facilitate the mounting of the arms and latch 42 on the axles 62. The openings or holes 70 provided in the arms 68 create points at which the thumb latch 42 can pivot back and forth or up and down, with the downwardly direction limited by the engagement of the lip 72 with the stop pedestals 60 (FIG. 10) as previously described.

Figure 15:
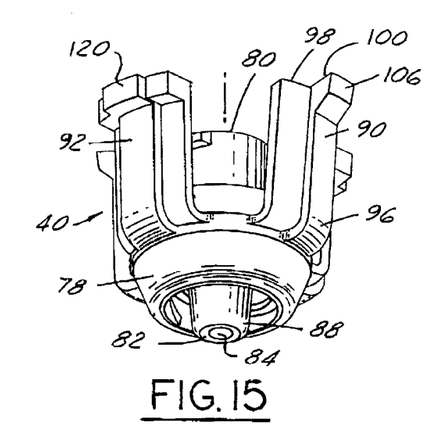
FIG. 15 is a perspective view of the generally cylindrical internal washer, arms, protrusions and the Luer Lock couplings.
Figure 16:
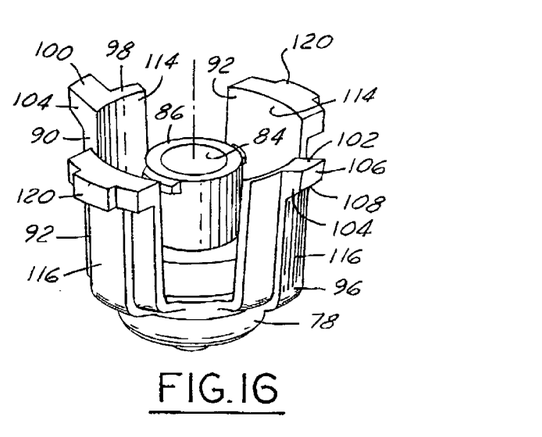
FIG. 16 is another perspective view of the washer assembly of FIG. 15 looking downwardly on the assembly and illustrating the relationship between the spaced apart arms, protrusions and the Luer Lock couplings.

The improved and novel washer assembly 40 as best illustrated in FIGS. 15 and 16 is of generally cylindrical configuration and is telescopically moveable within the cylinder 16 along the longitudinal axis 18. The washer 40 has a unitary body 78, first side 80 and a second side 82. A centrally located passage 84 of varying diameter extends through the washer body 78 between the first and second sides 80 and 82. The washer assembly 40 includes a first coupling means 86 through which the centrally located passage 84 extends. The coupling 86 is in the form of a Luer Lock type coupling which is standardized by the International Standards Organization and by the American Standards National Institute to fit all type Luer-Lock and Luer-slip tip syringes. The passage 84 may be non-threaded in accordance with the aforementioned standards or threaded to fit certain other types of syringes.

The washer 40 further includes a second coupling means 88 in the form of a Luer Lock type coupling with the internal passage 84 also extending therethrough. This passage 84 as mentioned previously is aligned with the passage in the first coupling 86. The passage 84 in the second coupling 88 of the Luer Lock construction is non-threaded although in certain cases it may be threaded to fit other types of needles. Both couplings 86 and 88 are Luer Lock couplings in accordance with the aforementioned standards. The second coupling 88 is designed to carry the needle 14 as best illustrated in FIGS. 8–11 inclusive.

The cylinder 16 is provided with two pairs of channels 85, which are approximately 90° apart on the interior surface 87 thereof. Each channel 85 is formed or grooved into the interior surface 87 of the cylinder 16 as best illustrated in FIGS. 8–11. The channels 85 extend from one end of the cylinder 16 to near the other end. The purpose of the channels 85 is to provide a guide or guide means between the cylinder 16 and the washer 40 for maintaining the orientation of the washer 40 and the cylinder 16 as best illustrated in FIGS. 9–11 inclusive as will be subsequently described.

The washer assembly 40 further includes a first pair of arms 90 and a second pair of arms 92. The arms of each pair of arms are located 180° apart as best illustrated in FIG. 16. An arm of one pair of arms is located 90° from the arms of the other pair of arms as best shown in FIG. 16.

The arms 90 of the first pair are integrally attached to the washer body 78 at the lower ends thereof 96. The upper ends 98 of the first pair of arm 90 are provided with outwardly extending protrusions or buttons 100. Each button or protrusion 100 of the first pair of arms 90 has a top surface 102, a pair of side surfaces 104 which are flat and parallel, an outer surface 106 and a bottom surface 108.

The upper half of the cylinder 16 is provided with a first pair of elongated openings 112 which extend completely through the cylindrical wall 16. The openings 112 are elongated and of generally rectangular cross section. Such openings 112 are located approximately 180° apart for receiving the outwardly extending protrusions or buttons 100 of the first pair of arms 90 thereby preventing movement of the washer 40 towards the lower end of the cylinder 16 when viewed in FIG. 10 thus preventing the washer 40, syringe 12 and needle 14 from exiting the cylinder 16 when the spring means or compression spring 38 is activated and thereby applies an upward thrust to the washer 40. The top surfaces 102 of the protrusions or buttons 100 are angled upwardly to facilitate the movement of the protrusions 100 into the corresponding elongated openings 112 in the cylinder wall 16 to thereby assist in catching and holding the washer 40 in position in the elongated openings 112. The bottom surfaces 108 of the protrusions 100 of the first pair of arms 90 are inclined upwardly as viewed in FIG. 16 to permit the washer 40 to move towards the bottom wall 50 of the cylinder 16 without catching in the elongated openings 112. Each arm 90 and 92 has inner and outer cylindrical surfaces 114 and 116.

It should be understood that the elongated openings 112 provided in cylinder 16 are offset from the center, with the protrusions 100 of the first pair of arms 90 being offset from the centerline of each arm 90 as best illustrated in FIG. 16.

The arms 92 of the second pair of arms are symmetrical about the centerline of each arm. The upper end of each arm has a centrally located protrusion or button 120 and inner cylindrical surface 122 and an outer cylindrical surface 124. The top surface, side surfaces, outer surface, and bottom surface of each protrusion 120 are flat. With such a construction, the top and bottom surfaces are parallel, the side surfaces are parallel and the outer surface is cylindrical.

The cylinder 16 further includes a second pair of openings in the form of inverted T-shaped slots 126. The slots 126 are located in the upper portion of the cylinder 16 and are located 180° apart. The inverted T-shaped slots 126 are constructed and arranged to receive the protrusions or buttons 120 provided on the second pair of arms 92 when the washer 40 is in the upper portion of the cylinder 16 as viewed in FIG. 11. At such time the protrusions 120 fill the T-shaped slot 126. The purpose of the protrusions 120 is to stop downward movement and the unlocking of the washer 40 when required. In addition, means are provided for urging the protrusions 120 inwardly to disengage same from the slots 126 so that downward movement of the washer 40 can occur.

The cylinder 16 adjacent the upper end of the cylinder immediately below the oval entrance 44 is provided with a pair of elongated flexible release arms 130. The arms 130 overlie the T-slots 126. The free end 132 of each arm 126 is provided with a rounded bulge or formation opposite the protrusions 120 when in the locked position as viewed in FIG. 11. When it is required to release the washer 40, pressure is applied to the flexible release arms 130 so as to move the formations 132 inwardly against the protrusions 120 of the second pair of arms 92 to thereby disengage the protrusions 120 from the T-shaped slots 126. Thereafter, pressure may be manually applied to the syringe 12 by moving the plunger 26 downwardly from the position illustrated in FIGS. 10 and 11 to the positions illustrated in FIGS. 8 and 9 . This results in the washer 40, syringe 12 and needle 14 moving downwardly into the bottom of the cylinder 16 where the syringe 12 is locked in the down position by the thumb latch 42 as illustrated in FIG. 8. At such time, the compression spring 38 is compressed as viewed in FIGS. 8 and 9 between the bottom portion of the washer assembly and the spring seat 56.

The release arms 130 and cylinder 16 are molded an integral unit from plastic material taken from the group of plastics including polypropylene and Nylon. As mentioned previously, the cylinder 16 is made from a clear plastic material which permits viewing of the syringe 12 including the graduations 36 and the amount of medications remaining in the syringe.

With the washer construction just described, it should be noted that all four arms 90 and 92 assist or aid in the stopping of the upward movement of the syringe 12 while still maintaining the orientation of the washer 40. This is accomplished by the outer tips or ends of the protrusions or buttons 100, 120 being seated in the channels 85 and moving upwardly or downwardly in the channels 85. The arms 90 of the first pair of arms and the corresponding protrusions or buttons 100 which cooperate with the elongated openings 112 provided in the cylinder 116 are designed primarily to stop upward movement. As mentioned previously, the buttons 100 are angled upwardly to allow a better attachment, catch and to hold the washer 40 in the openings 112. This keeps the washer 40, syringe 12 and needle 14 from exiting the main housing unit or cylinder 16 when the spring 38 is activated and upward thrust is applied to the washer 40. As also mentioned previously, the underside or bottom surface 108 of protrusions or buttons 100 are also angled upwardly to allow easy downward movement of the washer 40 without hanging in the elongated holes 112. Such holes 112 are offset from the center position of the inner channels 85. This has been done to eliminate an extra step in the manufacturing of the dies for this product. The protrusions or buttons 100 on the ends of the arms 90 are the only elements that are offset on the washer 40. It will be appreciated that the channels 85 for the arms 90 have also been modified to match the position of the buttons 100 within the main housing unit or cylinder 16.

In further summary of the invention, the second set of arms 92 and the corresponding protrusions or buttons 120 are utilized for stopping downward movement and also unlocking the washer 40 so downward movement can thereafter occur. When the protrusions 120 are set into the T-shaped slots 126, which are located on both sides of the main housing unit 16, the protrusions 120 keep the washer 40 from being pushed down into the bottom of the main housing unit or cylinder 16. However, when the pressure is applied inwardly by the thumb and index finger on the release arms 126, the buttons 120 are flexibly forced inwardly, disengaging themselves from their seated position within the slots 126. This allows or permits manual pressure to be applied by the operator to move the washer 40, syringe 12 and needle 14 downward into the bottom of the main housing unit 16, where the combination of the washer, syringe and needle are locked in the down position by the novel thumb latch 42. At this point, injections can be performed. It should be noted that the needle 14 does not need to be attached to the washer for this process to take place. It will generally be attached to the washer 40 after the abovementioned steps have been completed.

It will be observed that the flexible release arms 130 overlie the T-shaped slots 126 so that when they are pushed inwardly against the protrusions 120, release of the washer 40 from its seated position is achieved. The release arms 130 are the means by which the entire device is unlocked and prepared for injection use. The release arms 130 have a slightly rounded bulge or formation 132 on their inner ends created for comfort and for added torque when pressure is applied by the fingers of the operator. The release arms 130 are molded into the main housing unit or cylinder 16 and are able to flex inwardly and outwardly to a point needed to cause release or locking depending on the desired setting.

The washer 40 is equipped with the Luer Lock, Luer-Slip male and female attachments that are standardized by the International Standards Organization and the American Standards National Institute to fit all Luer Lock and Luer-Slip tipped syringes. The use of such standards assist in providing a fully automated retractable safety syringe.

The oval end 44 of the cylinder 16 is provided with a pair of reinforcing ribs 140 (FIG. 3) which are located on opposite sides of the enlarged opening on the interior surface thereof. The reinforcing ribs 140 as illustrated in FIG. 8 also serve as stops to prevent the syringe 12 from moving downwardly. Such ribs 140 also assist in preventing the syringe 12 from crushing the compression spring 38.

It will now be apparent that the medical technicians or operators can use a needle protection holder 10 with one hand allowing the technicians the freedom to perform other tasks with their other hands. The holder 10 is designed to protect medical technicians and personnel from exposures to infectious diseases. The holder 10 is designed to accept more than one type of syringe and to meet national standards. In operation or use, once the needle is placed in the body of a patient or animal using the needle protection holder 10, the needle 14 will never contact the open air, another patient or the technician unless the technician takes a direct action to unlock the assembly in the manner described previously. It would be appreciated that the holder 10 could be reused.

Earlier devices which have claimed to isolate the needle after use have certain drawbacks or restrictions. Some devices require you to use all the contents of the syringe before it retracts the needle into the provided enclosure. Still others are made to be used only with the manufacturer's syringes which limits the ability of hospitals or clinics to choose to purchase the type of syringe which best suits their purpose and budget.

Thus, with the present invention the holder 10 provides choices for the medical technicians and for the hospitals. Medical personnel can choose what syringe to use with the present invention, where and when to retract the needle and whether or not the needle protection holder is to be used again. The holder permits it to be used in the same manner as a Luer Lock syringe would normally be used, with the additional ability to protect all medical personnel from deadly needle sticks or punctures.

It will be further understood that the embodiment of the invention described herein is to be taken as a preferred example of the same and that various changes in size, shape and arrangement of parts may be resorted to without departing from the spirit of the invention or the scope of the claims which follow. Further, while the principles of the invention have now been made clear, there will be immediately obvious to those skilled in the art certain modifications of structure, arrangement, proportions, elements, materials and other components used in the practice of the invention which are particularly adapted for specific environments and operating requirements without departing from those principles.

What I claim is:

1. A needle protection holder to be interposed between a hypodermic syringe and a needle, said holder comprising:

a cylinder having a longitudinal axis surrounded by a cylinder wall;

said cylinder being open at one end and having a bottom wall at the other end;

said one end of said cylinder being enlarged to provide an entrance for the hypodermic syringe;

said cylinder adjacent said one end being provided with a pair of stop pedestals on the exterior surface of said cylinder wall;

a pair of spaced apart axles carried by said cylinder wall and located below said stop pedestals;

a washer of generally cylindrical configuration telescopically movable in the interior of said cylinder along said longitudinal axis;

said washer having first and second sides;

a centrally located passage in said washer between said first and second sides;

first coupling means fixed to the first side of said washer for attachment to the hypodermic syringe;

second coupling means fixed to the second side of said washer for attachment to the needle;

guide means interposed between said cylinder and said washer for maintaining the orientation of said washer in said cylinder;

spring means interposed in said cylinder between said bottom wall of said cylinder and said second side of said washer for biasing said washer and the needle carried thereby towards said one end of said cylinder; and a thumb latch having a lip opposite said longitudinal axis and a pair of spaced apart arms rotatably carried by said axles;

said thumb latch when rotated in one direction about said axles towards said longitudinal axis causing said lip to engage the syringe and thereby retain and latch the syringe within said cylinder.

2. The needle protection holder of claim 1 wherein said washer has first and second pairs of arms, each arm being integrally connected on one end to said washer, said first pair of arms being located 180° apart, said second pair of arms being located 180° apart, each arm of said first pair of arms at the other end being provided with an outwardly extending protrusion;

said cylinder wall between said ends having a pair of elongated openings for receiving said outwardly extending protrusions of said first pair of arms thereby preventing movement of said washer towards said one end of said cylinder and preventing said washer and the syringe and needle from exiting said cylinder when said spring means is activated and an upward thrust is applied to said washer.

3. The needle protection holder of claim 2 wherein each of said arms of said second pair has a center line, said second arms having outwardly projecting protrusions which are symmetrically arranged on the center lines of said second arms;

said cylinder wall between said ends having a second pair of elongated openings for receiving the protrusions on said second arms for stopping downward movement and unlocking of the washer when required so that downward movement of the washer can occur.

4. The needle protection holder defined in claim 3 wherein said second pair of elongated openings in said cylinder wall are in the form of T-shaped slots, said protrusions of said second pair of arms when received in said T-shaped slots preventing said washer from being pushed downwardly into the bottom of said cylinder.

5. The needle protection holder defined in claim 4 wherein said cylinder is provided with a pair of elongated flexible release arms which overly said T-shaped slots, said release arms when inward pressure is applied thereto engaging said protrusions of said second pair of arms to disengage said protrusions from said T-shaped slots thereby permitting manual pressure to be applied to the syringe to move the washer, syringe and needle downwardly into the bottom of the cylinder, where the syringe is locked in the down position by said thumb latch.

6. The needle protection holder defined in claim 5 wherein said release arms and cylinder are molded as an integral unit from plastic material.

7. The needle protection holder as defined in claim 6 wherein said cylinder is made from a clear plastic material which permits viewing of the syringe.

8. The needle protection holder defined in claim 2 wherein each of said protrusions of said first pair of arms has a top surface, a pair of side surfaces, an outer surface and a bottom surface;

said top surfaces being angled upwardly to facilitate the movement of the protrusions into the corresponding elongated openings in said cylinder wall and thereby catch and hold the washer in position in said elongated opening.

9. The needle protection holder defined in claim 8 wherein said bottom surfaces of the protrusions of said first pair of arms are inclined upwardly to permit said washer to move towards said bottom wall of said cylinder without catching in said elongated opening.

10. The needle protection holder defined in claim 2 wherein said elongated openings are offset from the center;

said protrusions of said first pair of arms being offset from the center line of said first pair of arms.

11. The needle protection holder as defined in claim 1 wherein said thumb latch is provided with an integral downwardly extending spring located between said spaced apart arms, said spring being engageable with the exterior surface of said cylinder wall and providing a pressure on said thumb latch so that the locking of the syringe in the down position can take place.

12. The needle protection holder defined in claim 11 wherein said thumb latch including said arms, lip and spring are molded as an integral unit from a plastic material.

13. The needle protection holder defined in claim 12 wherein said plastic material is taken from the group of plastics including polypropylene and nylon.

14. The needle protection holder defined in claim 11 wherein said spring means is flat and of generally rectangular cross-section and glides on the exterior surface of said cylinder.

15. The needle protection holder defined in claim 1 wherein said axles are aligned directly under the lip of said thumb latch.

16. The needle protection holder defined in claim 15 wherein the arms of said thumb latch are provided with openings, said arms when pressure is applied thereto, causing said openings to receive said axles.

17. The needle protection holder of claim 16 wherein the inner edges of said arms are beveled to remove material and thereby facilitate the mounting of said thumb latch on said axles.

18. The needle protection holder defined in claim 1 wherein said first coupling means is a Luer Lock type coupling with an internally threaded passage therethrough which is aligned with said centrally located passage in said washer.

19. The needle protection holder defined in claim 18 wherein said second coupling means is a Luer Lock type coupling with an internally threaded passage therethrough which is aligned with the centrally located passage in said washer.

20. The needle protection holder defined in claim 1 wherein said thumb latch when rotated in the opposite direction away from said longitudinal axis about said axles cause said lip to disengage from the syringe and the thumb latch to move away from said cylinder in an amount limited by the engagement of said thumb latch with said stop pedestals.

21. The needle protection holder defined in claim 1 wherein said thumb latch has a curved surface for a person's thumb when operating the latch, said lip being an integral part of said latch and being inclined downwardly towards the open end of said cylinder.

22. The needle protection holder defined in claim 1 wherein said stop pedestals are formed out of the walls of the cylinder holding said axles.

23. An apparatus comprising the combination of a hypodermic syringe, a needle and a needle protection holder, said needle protection holder comprising:
- a cylinder having a longitudinal axis surrounded by a cylinder wall;
- said cylinder being open at one end and having a bottom wall at the other end;
- said one end of said cylinder being enlarged to provide an entrance for said hypodermic syringe;
- said cylinder adjacent said one end being provided with a pair of stop pedestals on the exterior surface of said cylinder wall;
- a pair of spaced apart axles carried by said cylinder wall and located below said stop pedestals;
- a washer of generally cylindrical configuration telescopically movable in the interior of said cylinder along said longitudinal axis;
- said washer having first and second sides;
- a centrally located passage in said washer between said first and second sides;
- a first coupling means fixed to the first side of said washer and attached to said hypodermic syringe;
- a second coupling means fixed to the second side of said washer and attached to said needle;
- a guide means interposed between said cylinder and said washer for maintaining the orientation of said washer in said cylinder;
- a spring means interposed in said cylinder between said bottom wall of said cylinder and said second side of said washer for biasing said washer and said needle carried thereby towards said one end of said cylinder; and
- a thumb latch having a lip opposite said longitudinal axis and a pair of spaced apart arms rotatably carried by said axles;
- said thumb latch when rotated in one direction about said axles towards said longitudinal axis causing said lip to engage said syringe and thereby retain and latch said syringe within said cylinder.

24. A needle protection holder to be interposed between a hypodermic syringe and a needle, said holder comprising:
- a cylinder having a longitudinal axis surrounded by a cylinder wall;
- said cylinder being open at one end and having a bottom wall at the other end;
- a washer of generally cylindrical configuration telescopically movable in said cylinder along said longitudinal axis;
- said washer having a body with first and second sides and a cylindrical wall;
- a centrally located passage in said washer between said first and second sides;
- first coupling means fixed to one side of said washer for attachment to the hypodermic syringe;
- second coupling means fixed to the second side of said washer for attachment to the needle;
- said cylinder having inner and outer surfaces;
- said inner surface of said cylinder having thereon four elongated channels which are spaced apart;
- said cylinder having four elongated openings extending therethrough;
- said washer having four circumferentially spaced apart arms, with inner and outer cylindrical surfaces, said arms having one end connected to said body with the other ends of said arms being provided with radially outwardly extending buttons which are spaced apart, one button for each elongated opening, said buttons received by said channels for maintaining the orientation of said washer in said cylinder;
- spring means interposed in said cylinder between said bottom wall of said cylinder and said second side of said washer for biasing said washer and the needle carried thereby towards the open end of said cylinder; and
- latch means carried by the upper end of said cylinder for engagement with the syringe to retain the syringe within said holder.

25. The needle protection holder of claim 24 wherein said circumferential spaced apart arms are arranged in first and second pairs of arms, said first pair of arms being located 180° apart, said second pair of arms being located 180° apart, each arm of said first pair of arms at said other end being provided with said buttons;

said cylinder wall between said ends having a pair of said elongated openings for receiving said outwardly extending buttons of said first pair of arms thereby preventing movement of said washer towards said one end of said cylinder and preventing said washer and the syringe and needle from exiting said cylinder when said spring means is activated and an upward thrust is applied to said washer.

26. The needle protection holder of claim 25 wherein each of said arms of said second pair has a center line, said second arms having said outwardly projecting buttons which are symmetrically arranged on the center lines of said second arms;

said cylinder wall between said ends having a second pair of elongated openings for receiving said buttons on said second arms for stopping downward movement and unlocking of the washer when required so that downward movement of the washer can occur.

27. The needle protection holder defined in claim 26 wherein said second pair of elongated openings in said cylinder wall are in the form of T-shaped slots, said buttons of said second pair of arms when received in said T-shaped slots preventing said washer from being pushed downwardly into the bottom of said cylinder.

28. The needle protection holder defined in claim 27 wherein said cylinder is provided with a pair of elongated flexible release arms which overly said T-shaped slots, said release arms when inward pressure is applied thereto engaging said buttons of said second pair of arms to disengage said buttons from said T-shaped slots thereby permitting manual pressure to be applied to the syringe to move the washer, syringe and needle downwardly into the bottom of the cylinder, where the syringe is locked in the down position by said latch means.

29. The needle protection holder defined in claim 28 wherein said release arms and cylinder are molded as an integral unit from plastic material.

30. The needle protection holder defined in claim 25 wherein each of said buttons of said first pair of arms has a top surface, a pair of side surfaces, an outer surface and a bottom surface;

said top surfaces being angled upwardly to facilitate the movement of the buttons into the corresponding elongated openings in said cylinder wall and thereby catch and hold the washer in position in said elongated opening.

31. The needle protection holder defined in claim 30 wherein said bottom surfaces of said buttons of said first pair of arms are inclined upwardly to permit said washer to move towards said bottom wall of said cylinder without catching in said elongated opening.

32. The needle protection holder defined in claim 25 wherein said elongated openings are offset from the center; said buttons of said first pair of arms being offset from the center line of said first pair of arms.

33. The needle protection holder defined in claim 24 wherein said cylinder adjacent said one end being provided with a pair of stop pedestals on the exterior surface of said cylinder wall;

a pair of spaced apart axles carried by said cylinder wall and located below said top pedestals;

said latch means having a body provided with a lip opposite said longitudinal axis and a pair of spaced apart arms rotatably carried by said axles;

said latch means when rotated in one direction about said axles towards said longitudinal axis causing said lip to engage the syringe and thereby retain and latch the syringe within said cylinder.

34. The needle protection holder as defined in claim 33 wherein the body of said latch means is provided with an integral downwardly extending spring located between said spaced apart arms, said spring being engageable with the exterior surface of said cylinder wall and providing a pressure on said latch means so that the locking of the syringe in the down position can take place.

35. The needle protection holder defined in claim 34 wherein the body of said latch means including said arms, lip and spring are molded as an integral unit from a plastic material.

36. The needle protection holder as defined in claim 35 wherein said plastic material is taken from the group of plastics including polypropylene and nylon.

37. The needle protection holder as defined in claim 34 wherein said spring is flat and of generally rectangular cross-section and glides on the exterior surface of said cylinder.

38. The needle protection holder defined in claim 33 wherein said axles are aligned directly under the lip of said latch means.

39. The needle protection holder defined in claim 38 wherein the arms of said latch means are provided with openings, said arms when pressure is applied thereto, causing said openings to receive said axles.

40. The needle protection holder of claim 39 wherein the inner edges of said arms are beveled to remove material and thereby facilitate the mounting of the body of said latch means on said axles.

41. The needle protection holder defined in claim 33 wherein said latch means when rotated in the opposite direction away from said longitudinal axis about said axles cause said lip to disengage from the syringe and the latch means to move away from said cylinder in an amount limited by the engagement of said latch means with said stop pedestals.

42. The needle protection holder defined in claim 33 wherein the body of said latch means has a curved surface for a person's thumb when operating the latch means, said lip being an integral part of said latch means and being inclined downwardly towards the open end of said cylinder.

43. The needle protection holder defined in claim 33 wherein said stop pedestals are formed out of the walls of cylinder holding said axles.

44. The needle protection holder as defined in claim 33 wherein said cylinder is made from a clear plastic material which permits viewing of the syringe.

45. The needle protection holder defined in claim 24 wherein said first coupling means is a Luer Lock type coupling with an internally threaded passage therethrough which is aligned with said centrally located passage in said washer.

46. The needle protection holder defined in claim 24 wherein said second coupling means is a Luer Lock type coupling with an internally threaded passage therethrough which is aligned with the centrally located passage in said washer.

47. An apparatus comprising the combination of a hypodermic syringe, a needle and a needle protection holder, said needle protection holder comprising:

a cylinder having a longitudinal axis surrounded by a cylinder wall;

said cylinder being open at one end and having a bottom wall at the other end;

a washer of generally cylindrical configuration telescopically movable in the interior of said cylinder along said longitudinal axis;

said washer having a body with first and second sides and a cylindrical wall;

a centrally located passage in said washer between said first and second sides;

a first coupling means fixed to the first side of said washer and attached to said hypodermic syringe;

a second coupling means fixed to the second side of said washer and attached to said needle;

said cylinder having inner and outer surfaces;

said inner surface of said cylinder having thereon four elongated channels which are spaced apart;

said cylinder having four elongated openings extending therethrough;

said washer having four circumferentially spaced apart arms, with inner and outer cylindrical surfaces, said arms having one end connected to said body with the other ends of said arms being provided with radially outwardly extending buttons which are spaced apart, one button for each elongated opening, said buttons received by said channels for maintaining the orientation of said washer in said cylinder;

a spring means interposed in said cylinder between said bottom wall of said cylinder and said second side of said washer for biasing said washer and said needle carried thereby towards the open end of said cylinder; and a latch means carried by the upper end of said cylinder which engages said syringe to retain said syringe within said holder.

* * * * *